United States Patent
Magnuson et al.

(10) Patent No.: US 8,934,603 B2
(45) Date of Patent: Jan. 13, 2015

(54) SYSTEMS AND METHODS FOR DETECTING CONTRABAND USING QUADRUPOLE RESONANCE AND X-RAY DETECTION

(71) Applicant: Morpho Detection, Inc., Newark, CA (US)

(72) Inventors: Erik Edmund Magnuson, Cardiff, CA (US); Christopher W. Crowley, San Diego, CA (US); Alejandro Pedro Bussandri, La Jolla, CA (US)

(73) Assignee: Morpho Detection, LLC, Newark, CA (US)

( * ) Notice: Subject to any disclaimer, the term of this patent is extended or adjusted under 35 U.S.C. 154(b) by 136 days.

(21) Appl. No.: 13/798,515

(22) Filed: Mar. 13, 2013

(65) Prior Publication Data
US 2014/0270066 A1 Sep. 18, 2014

(51) Int. Cl.
*G01N 23/04* (2006.01)
*G01R 33/48* (2006.01)

(52) U.S. Cl.
CPC ................... *G01R 33/4812* (2013.01)
USPC ............................................. 378/57; 324/300

(58) Field of Classification Search
USPC ................. 378/57, 63; 324/300–322
See application file for complete search history.

(56) References Cited

U.S. PATENT DOCUMENTS

| | | | |
|---|---|---|---|
| 7,292,030 B2 | 11/2007 | Laubacher | |
| 7,366,281 B2 * | 4/2008 | Skatter | 378/57 |
| 7,609,807 B2 | 10/2009 | Leue et al. | |
| 7,750,631 B2 | 7/2010 | Crowley | |
| 7,839,979 B2 | 11/2010 | Hauttmann et al. | |
| 2007/0035295 A1 | 2/2007 | Laubacher | |
| 2007/0200566 A1 * | 8/2007 | Clark et al. | 324/318 |
| 2007/0229069 A1 * | 10/2007 | Laubacher | 324/300 |
| 2011/0102597 A1 | 5/2011 | Daly et al. | |
| 2013/0336447 A1 * | 12/2013 | Morton | 378/57 |

* cited by examiner

*Primary Examiner* — Hoon Song
(74) *Attorney, Agent, or Firm* — Armstrong Teasdale LLP

(57) ABSTRACT

A contraband detection system is provided. The contraband detection system includes an X-ray system including a front X-ray transmitter/detector and a rear X-ray transmitter/detector. The contraband detection system further includes a quadrupole resonance (QR) system comprising a first QR coil, and a second QR coil, wherein the first and second QR coils are located between the front and rear X-ray transmitter/detectors, and wherein the first and second QR coils are constructed from a material having a low mass attenuation coefficient and a high conductivity such that the first and second QR coils do not substantially interfere with transmitting X-rays and detecting emitted photons using the X-ray system. The contraband detection system further comprise a computing device coupled to the X-ray system and the QR system, the computing device configured to detect contraband based on signals received from the X-ray system and the QR system.

20 Claims, 4 Drawing Sheets

SYSTEMS AND METHODS FOR DETECTING CONTRABAND USING QUADRUPOLE RESONANCE AND X-RAY DETECTION

BACKGROUND

The embodiments described herein relate generally to detecting contraband, and more particularly, to detecting contraband using a system that combines X-ray detection and quadrupole resonance (QR) detection.

At least some known passenger screening systems detect contraband. As used herein, the term "contraband" refers to illegal substances, explosives, narcotics, weapons, a threat object, and/or any other material that a person is not allowed to possess in a restricted area, such as an airport. The contraband detection involves a combination of sensors and structures to control a flow of passengers. Although passengers are referred to herein, any person and/or object (i.e., subject) may be scanned using the systems and methods described herein.

For example, one known checkpoint system first screens passengers with a whole-body walk-through metal detector (WTMD). In such a checkpoint system, when a threat item or anomaly is detected from a whole body scan, the passenger is directed to a wanding station, which is a physical structure that controls the progress of the passenger. Importantly, if a threat item or anomaly is detected by the whole body scan, then the passenger may be considered a threat. As such, his or her mobility is controlled by the structure of the wanding station. Within that controlled structure, or at its egress, a security officer can use a detection wand to perform a localized scan of the passenger's body to resolve the alarm. If the passenger is then cleared, he or she may proceed beyond the physical structures of the wanding area. However, there are limits to such systems.

BRIEF SUMMARY

In one aspect, a contraband detection system is provided. The contraband detection system includes an X-ray system including a front X-ray transmitter/detector and a rear X-ray transmitter/detector, wherein the front and rear X-ray transmitter/detectors are each configured to at least one of transmit X-rays and detect emitted photons to generate at least one image of a subject standing in a subject region. The contraband detection system further includes a quadrupole resonance (QR) system comprising a first QR coil, and a second QR coil, wherein the first and second QR coils are located between the front and rear X-ray transmitter/detectors, and wherein the first and second QR coils are constructed from a material having a low mass attenuation coefficient and a high conductivity such that the first and second QR coils do not substantially interfere with transmitting X-rays and detecting emitted photons using the X-ray system. The contraband detection system further comprise a computing device coupled to the X-ray system and the QR system, the computing device configured to detect contraband at the subject region based on signals received from the X-ray system and the QR system.

In another aspect, a security scanner for detecting contraband located in or on a subject standing in a subject region is provided. The security scanner includes a front X-ray transmitter/detector, a rear X-ray transmitter/detector, wherein the front and rear X-ray transmitter/detectors are each configured to at least one of transmit X-rays and detect emitted photons to generate at least one image of the subject, a first QR coil, and a second QR coil, wherein the first and second QR coils are located between the front and rear X-ray transmitter/ detectors, and wherein the first and second QR coils are constructed from a material having a low mass attenuation coefficient and a high conductivity such that the first and second QR coils do not substantially interfere with transmitting X-rays and detecting emitted photons using the front and rear X-ray transmitter/detectors.

In yet another aspect, a method for detecting contraband located on or in a subject is provided. The method includes scanning the subject using an X-ray system, wherein the X-ray system includes a front X-ray transmitter/detector and a rear X-ray transmitter/detector, the front and rear X-ray transmitter/detectors each configured to at least one of transmit X-rays and detect emitted photons to generate at least one image of the subject. The method further includes scanning the subject using a quadrupole resonance (QR) system, wherein the QR system includes a first QR coil, and a second QR coil, wherein the first and second QR coils are located between the front and rear X-ray transmitter/detectors, and wherein the first and second QR coils are constructed from a material having a low mass attenuation coefficient and a high conductivity such that the first and second QR coils do not substantially interfere with transmitting X-rays and detecting emitted photons using the X-ray system, and detecting whether contraband is present based on at least one of the X-ray scan and the QR scan.

DETAILED DESCRIPTION

The systems and methods described herein enable scanning a subject using both an X-ray system and a quadrupole resonance (QR) system. The X-ray system and QR system can both be implemented in the same security scanner. Because QR coils in the QR system are constructed from materials having a low mass attenuation coefficient and a high conductivity, the QR coils do not substantially interfere with operation of the X-ray system. The security scanner also includes shield panels that shield the QR coils from external interference.

Figure 1:
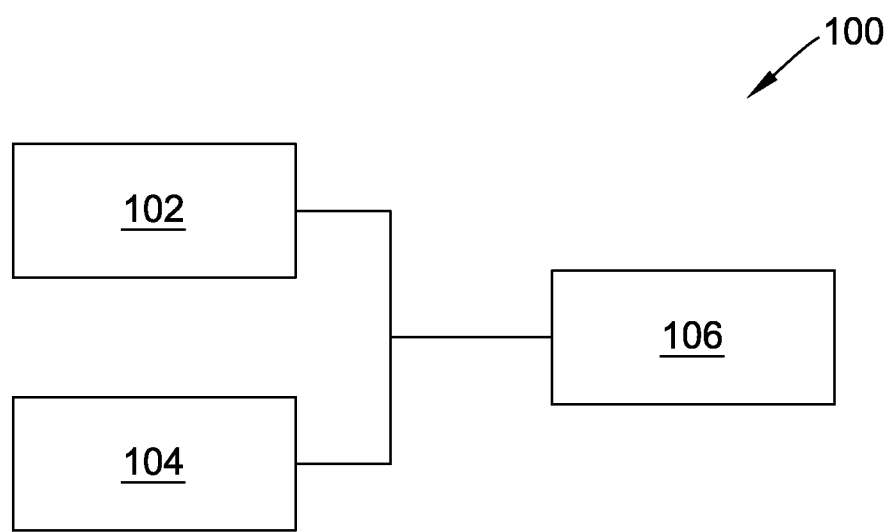
FIG. 1 is a block diagram of an exemplary detection system.

FIG. 1 is a block diagram of an exemplary detection system 100 that includes an X-ray system 102 and a quadrupole resonance (QR) system 104. In the exemplary embodiment X-ray system 102 and QR system 104 are communicatively coupled to a computing device 106 to facilitate screening one or more subjects for contraband. Further, in the exemplary embodiment, X-ray system 102 is an X-ray backscatter system. Alternatively, X-ray system 102 may be an X-ray transmission system.

As used herein, the term "contraband" refers to illegal substances, explosives, narcotics, weapons, special nuclear materials, dirty bombs, nuclear threat materials, a threat object, and/or any other material that a person is not allowed to possess in a restricted area, such as an airport. Contraband may be hidden within a subject (e.g., in a body cavity of a subject) and/or on a subject (e.g., under the clothing of a subject).

Although X-ray backscatter technology is capable of detecting contraband on a subject, X-ray backscatter technology is relatively ineffective at detecting contraband within a subject. X-ray backscatter systems may also include one or more privacy filters that inhibit detecting contraband in sensitive areas of a subject (e.g., in and/or near a groin of the subject). Further, QR technology is capable of detecting contraband on and/or in a subject, but may only be effective at detecting materials that have a detectable response to a radiofrequency (RF) magnetic field. Accordingly, as detection system 100 includes X-ray system 102 and QR system 104, detection system 100 enables detecting contraband both within a subject and on a subject.

In the exemplary embodiment, computing device 106 detects contraband based on signals received from at least one of X-ray system 102 and QR system 104. For example, computing device 106 may perform one or more image analysis operations on the image data generated using X-ray system 102 and/or QR system 104, and/or an operator may visually inspect images displayed by computing device 106 for contraband. In at least some embodiments, computing device 106 is configured to identify predetermined shapes (e.g., sharp items indicative of blades) to detect contraband. Alternatively, computing device 106 may use other suitable methods to determine whether contraband is present.

If computing device 106 detects contraband, computing device 106 may generate an alert. The alert may include any audio and/or visual indication that notifies an operator of the potential presence of contraband. For example, the alert may include at least one of a sound generated by computing device 106 and/or an icon, symbol, and/or message displayed using computing device 106. Upon observing the alert, the operator may take appropriate action, such as detaining a subject being scanned by detection system 100.

Figure 2:
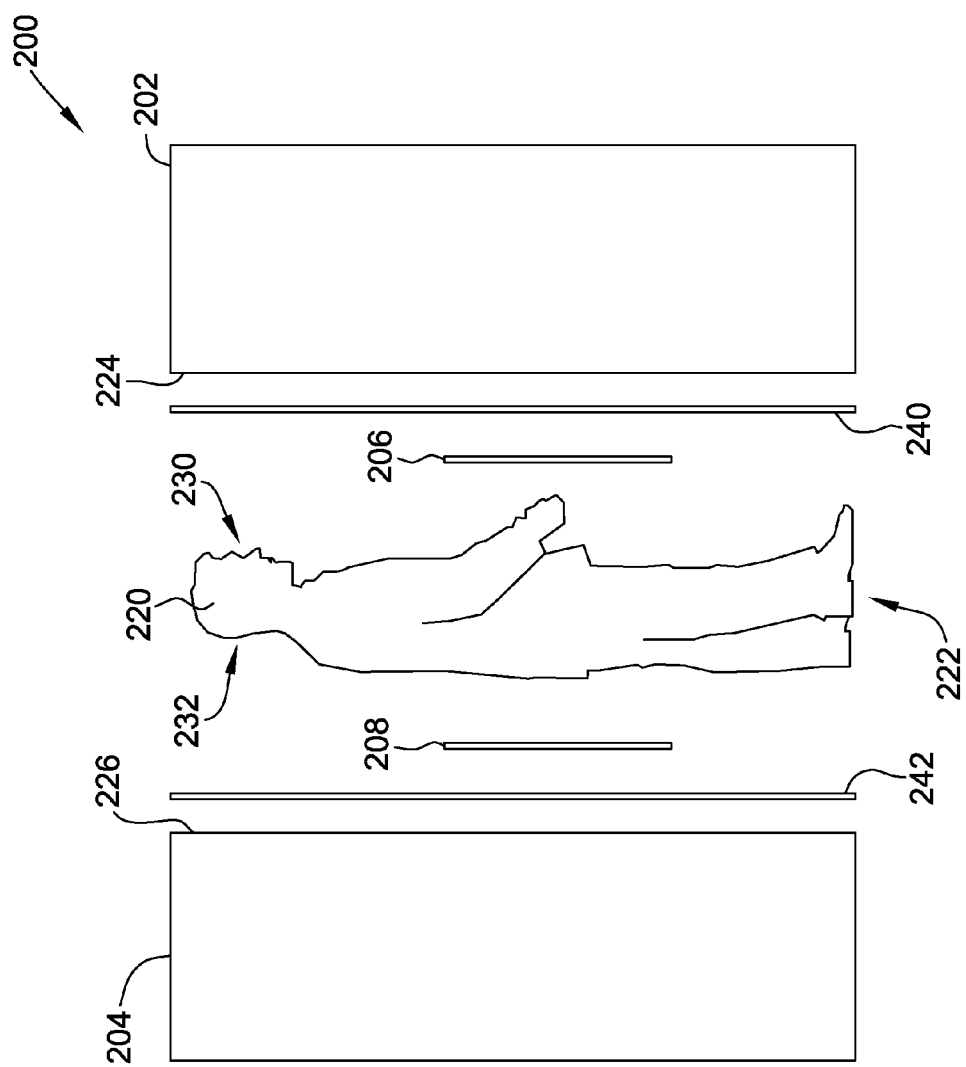
FIG. 2 is a schematic diagram of an exemplary security scanner.

FIG. 2 is a schematic diagram of an exemplary security scanner 200 that may be implemented in detection system 100 (shown in FIG. 1). Security scanner 200 includes a front X-ray transmitter/detector 202 and a rear X-ray transmitter/detector 204 that form at least part of X-ray system 102 (shown in FIG. 1). In the exemplary embodiment, where X-ray system 102 is a backscatter system, front and rear transmitter/detectors 202 and 204 each function as both a transmitter and a detector. In alternative embodiments, where X-ray system 102 is an X-ray transmission system, one of front and rear transmitter/detectors 202 and 204 functions as the X-ray transmitter, and the other of front and rear transmitter/detectors 202 functions as the detector.

Security scanner also includes a front QR coil 206 and a rear QR coil 208 that form at least part of QR system 104 (shown in FIG. 1).

Security scanner 200 scans a subject 220 for contraband. As shown in FIG. 2, in the exemplary embodiment, subject 220 stands in a subject region 222 located between front and rear X-ray transmitter/detectors 202 and 204 and between front and rear QR coils 206 and 208. More specifically, front QR coil 206 is located between subject region 222 and an interior face 224 of front X-ray transmitter/detector 202 that faces subject region 222. Rear QR coil 208 is located between subject region 222 and an interior face 226 of rear X-ray transmitter/detector 204 that faces subject region 222.

Planes of front and rear QR coils 206 and 208 are substantially parallel to interior faces 226 and 228 and substantially orthogonal to X-rays transmitted by front and rear X-ray transmitter/detectors 202 and 204, resulting in a relatively short distance for the transmitted X-rays to pass through front and rear coils 206 and 208. Auxiliary components of QR system 102 that may block or obscure contraband detection by X-ray system 102, such as capacitors, relays, or other articles (none shown in FIG. 2) are placed outside of a field of view of X-ray system 102 relative to subject 220, in the exemplary embodiment.

To scan subject 220 for contraband, in the exemplary embodiment, each of front and rear X-ray transmitter/detectors 202 and 204 transmits a plurality of X-rays towards subject 220. When the transmitted X-rays are absorbed by subject 220, photons are emitted (i.e., backscattered) from subject 220 back towards X-ray transmitter/detectors 202 and 204. The emitted photons are detected by X-ray transmitter/detectors 202 and 204, and using computing device 106 (shown in FIG. 1), images of subject 220 can be generated from the detected photons. Specifically, computing device generates an image of a front 230 of subject 220 based on photons detected by front X-ray transmitter/detector 202, and generates an image of a back 232 of subject 220 based on photons detected by rear X-ray transmitter/detector 204. From the generated images, it can be determined whether contraband is present on subject 220. In embodiments where X-ray system 102 is a transmission system, a single image of subject 220 is generated.

In the exemplary embodiment, subject 220 is also scanned for contraband using front and rear QR coils 206 and 208. Specifically, by running current through front and rear QR coils 206 and 208 in opposite directions (i.e., a clockwise direction in one coil, a counterclockwise direction in the other coil), a radio frequency (RF) magnetic field is generated between front and rear QR coils 206 and 208. Certain materials containing quadrupolar nuclei, such as certain explosive compounds, have a detectable response to the RF magnetic field generated between front and rear QR coils 206 and 208. Further, as QR system 104 uses RF modalities, QR system 104 can detect those materials non-invasively inside subject 220, not only external to subject 220. Accordingly, by monitoring a magnetic field detected by front and rear QR coils 206 and 208, in the exemplary embodiment, computing device 106 (shown in FIG. 1) determines whether materials with a detectable response are located on and/or in subject 220.

For QR detection, quadrupolar nuclei interacting with electric field gradients created by a local electron environment have quantized energy levels. In the presence of an RF magnetic field excitation, nuclear transitions are induced between the quadrupolar energy levels via the coupling between a nuclear magnetic dipole moment and a resonant time-dependent magnetic field. These microscopic nuclear transitions produce a time-dependent magnetization of the sample that generates a voltage in a nearby antenna (i.e., a QR signal). A QR detection system, such as QR system 104, typically includes an apparatus for generating the excitation RF magnetic field (i.e., a transmitter) as well as components for detecting and interpreting the induced QR signal (i.e., a receiver). In the exemplary embodiment of QR system 104, the front and rear coils 206 and 208 are used to transmit the RF magnetic field as well as to receive the QR signal.

Because security scanner 200 combines X-ray system 102 and QR system 104, complementary benefits of both systems can be achieved (i.e., internal screening using QR system 104 and external surface imaging using X-ray system 102). However, as QR coils 206 and 208 are located between subject 220 and X-ray transmitter/detectors 202 and 204, QR coils 206 could potentially interfere with the transmitted X-rays and the emitted photons of X-ray system 102, thus interfering with the ability of X-ray system 102 to facilitate accurately detecting contraband. Accordingly, while QR coils in at least some known QR detection systems are made of copper, in the exemplary embodiment, QR coils 206 and 208 are manufactured from a material having a relatively low mass attenuation coefficient and a relatively high conductivity. Notably, operation of X-ray system 102 does not substantially interfere with QR system 104.

Because of the relatively low mass attenuation coefficient of QR coils 206 and 208, the transmitted X-rays and the emitted photons are substantially unaffected when passing through QR coils 206 and 208. Further, because of the relatively high conductivity of QR coils 206 and 208, QR coils 206 and 208 can be relatively thin (also reducing interference with the transmitted X-rays and the emitted photons) and still conduct currents sufficient for detecting contraband.

In the exemplary embodiment, QR coils 206 and 208 are constructed using thin aluminum sheets such that QR coils 206 and 208 have a mass attenuation coefficient of 0.37 cm$^2$/g for 50 keV photons and a conductivity of $3.8 \times 10^7$ S/m. Advantageously, aluminum QR coils have a lower mass attenuation coefficient and require less mass for a given conductivity that copper QR coils used in at least some known QR systems, as described in more detail below. Alternatively, QR coils 206 and 208 may be constructed from any suitable material that avoids substantially interfering with X-ray system 102. For example, in one embodiment, QR coils 206 and 208 are constructed using carbon nanowires such that QR coils 206 and 208 have a mass attenuation coefficient of 0.16 cm$^2$/g for 50 keV photons and a conductivity of $3.0 \times 10^7$ S/m. Accordingly, carbon nanotubes may better conductivity than copper with a mass attenuation coefficient slightly higher than that of Beryllium.

The sensitivity of QR coils 206 and 208 is related to a signal to noise ratio (SNR) represented by a signal voltage to QR coils 206 and 208 divided by a noise voltage. With higher sensitivity, the SNR is improved for a given target mass (resulting in a lower false alarm rate by scanner 200), and the target mass needed to produce a given SNR is reduced. For QR coils 206 and 208, the signal voltage is fixed by the geometry of the coils. The noise voltage is proportional to the resistance of QR coils 206 and 208. Specifically, $$V_n = \sqrt{4kTRB} \quad \text{Equation (1)}$$

Where, $V_n$ is the noise voltage, k is Boltzman's constant, T is absolute temperature, R is resistance, and B is bandwidth. Temperature T and bandwidth B are fixed by the specific application, while resistance R is a function of the design and material of QR coils 206 and 208.

In the exemplary embodiment, QR coils 206 and 208 are sheet conductors. Accordingly, the resistance R (and thus noise voltage $V_n$) will decrease with increasing thickness up to a point where the sheet is between one and two skin depth's thick. The skin depth of aluminum is approximately 87 microns (μm) and the skin depth of copper is approximately 69 μm. Given that the specific gravity of aluminum is 2.7 and the specific gravity of copper is 8.9, one skin depth sheet of copper will weigh about 2.6 times as much as the same sheet size of one skin depth thick aluminum. Accordingly, aluminum QR coils, such as QR coils 206 and 208 in the exemplary embodiment, are significantly lighter than equivalent copper QR coils.

More specifically, the conductor of a sheet coil is typically made to be at least two skin depths thick at the lowest operating frequency as increasing thickness beyond that will not significantly improve conductivity. At 900 kHz, the skin depth of copper is 70 microns, two skin depths is thus 140 microns and with a density of 8.96 g/cc, the copper coil has an areal density of 0.125 g/cm$^2$. The mass attenuation coefficient for 50 keV photons is 2.6 cm$^2$/g with the product of the areal density and attenuation coefficient equaling 0.325. The un-attenuated portion is given by $e^{-0.325}$, which equals 0.72 (72%), which is significant reduction of X-ray intensity. An aluminum coil designed for two skin depths at 900 kHz would be 175 microns thick, and the resulting areal density would 0.047 g/cm$^2$. The un-attenuated portion is 98% at 50 keV photon energy, which is a barely noticeable reduction in photon intensity. Beryllium would give further reductions in attenuation, but with the disadvantages of slightly lower Q and the toxicity of Beryllium.

As a copper QR coil has about 2.6 times the mass per unit area as an aluminum QR coil with an equivalent skin depth, the attenuation of the copper coil will be at least 2.6 times that of the aluminum QR coil. Further, as copper has a higher atomic number than aluminum, the attenuation for a given mass per unit area will be higher for copper for photon energies less than 200 kilo-electronvolts (keV). For example, for photons at 70 keV, the mass attenuation coefficient for copper is more than three times that of aluminum, such that the attenuation through one skin depth of copper will be at least eight times that of aluminum.

Accordingly, as compared to the copper QR coils used in at least some known QR systems, the aluminum QR coils 206 and 208 in the exemplary embodiment are significantly more transparent to the transmitted X-rays and emitted photons from X-ray system 102. That is, in contrast to an embodiment of security scanner 200 using copper QR coils, aluminum QR coils 206 and 208 do not substantially affect transmitted X-rays and emitted photons. Embodiments using carbon nanowires for QR coils 206 and 208 are even more transparent to X-rays and photons than aluminum QR coils.

In the exemplary embodiment, security scanner 200 includes a first shield panel 240 and a second shield panel 242. First shield panel 240 is coupled to interior face 224 of front X-ray transmitter/detector 202, and second shield panel 242 is coupled to interior face 226 of rear X-ray transmitter/detector 204.

First and second shield panels 240 and 242 facilitate shielding front and rear QR coils 206 and 208 from external or background electromagnetic fields and radio frequency interferences. For example, far away sources (i.e., radio stations) and/or equipment in the vicinity of security scanner 200 (i.e., electronic equipment may cause radio frequency interferences. By shielding QR coils 206 and 208 using first and second shield panels 240 and 242, interference can be reduced, resulting in a lower false alarm rate by security scanner 200.

First and second shield panels 240 and 242 are substantially planar in the exemplary embodiment. Further, similar to QR coils 206 and 208, first and second shield panels 240 and 242 are constructed from materials having a relatively low mass attenuation coefficient and a relatively high conductivity, such as a material including aluminum and/or carbon nanowires.

In the exemplary embodiment QR coils 206 and 208 and shield panels 240 and 242 have a thickness in a range of 1/64" to 1/32". Alternatively, QR coils 206 and 208 and shield panels 240 and 242 may have any suitable thickness that enables security scanner 200 to function as described herein.

Figure 3:
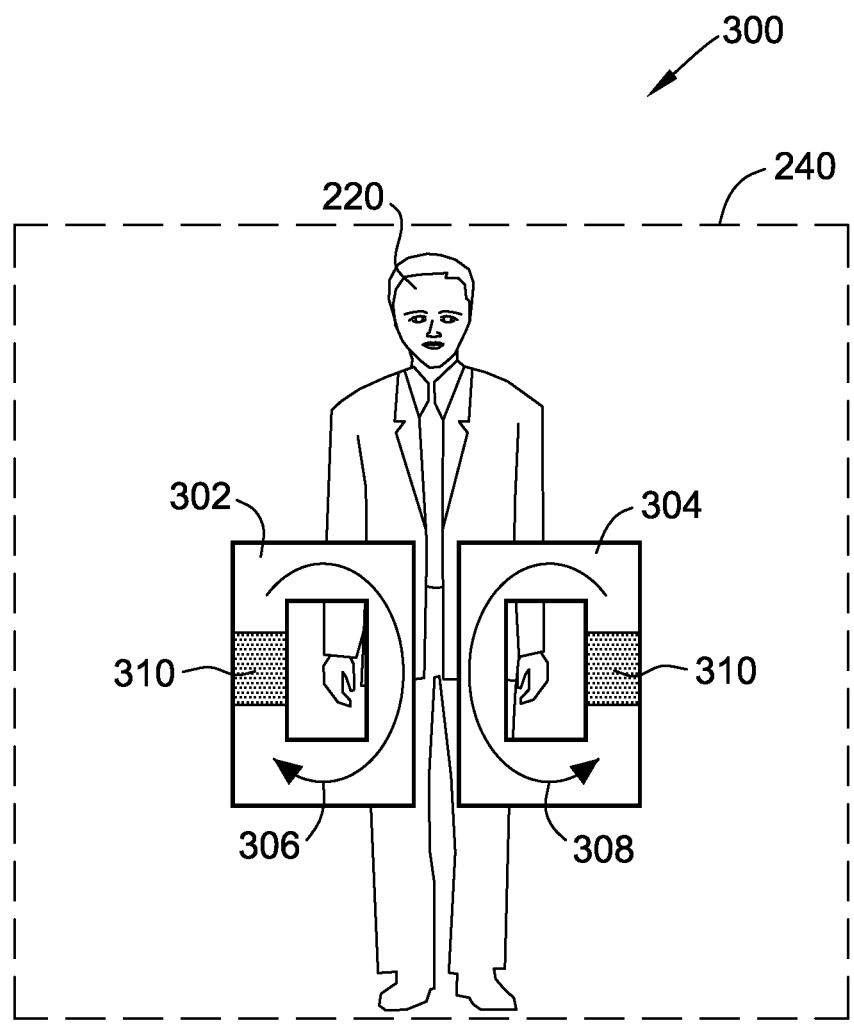
FIG. 3 is a schematic diagram of an alternative security scanner.

FIG. 3 is a schematic diagram of an alternative security scanner 300. Unless otherwise noted, security scanner 300 is substantially similar to security scanner 200 (shown in FIG. 2), and the same reference numerals are used herein. Unlike security scanner 200, in which front and rear QR coils 206 and 208 are located on either side of subject 220, in security scanner 300, a first QR coil 302 and a second QR coil 304 are both located on the same side (i.e., the front or back) of subject 220. That is, first and second QR coils 302 and 304 are either both located between subject 220 and front X-ray transmitter/detector 202, or both located between subject 220 and rear X-ray transmitter/detector 204. For clarity, second shield panel 242, and front and rear X-ray transmitter/detectors 202 and 204 are not shown in FIG. 4, and the outline of first shield panel 240 is shown.

In alternative security scanner 300, current is run though first and second QR coils 302 and 304 in opposite directions. That is, as shown in FIG. 3, current is run through first QR coil 302 in a clockwise direction 306, and current is run through second QR coil 304 in a counterclockwise direction 308. Alternatively, current may be run through first QR coil 302 in a counterclockwise direction and through second QR coil 304 in a clockwise direction. As shown in FIG. 3, ancillary components 310 of QR system 104 (shown in FIG. 1), such as capacitors and relays, are located outside a field of view that includes subject 220. According, ancillary components 310 do not obscure or inhibit the ability of X-ray system 102 to image subject 220 and to detect contraband.

Figure 4:
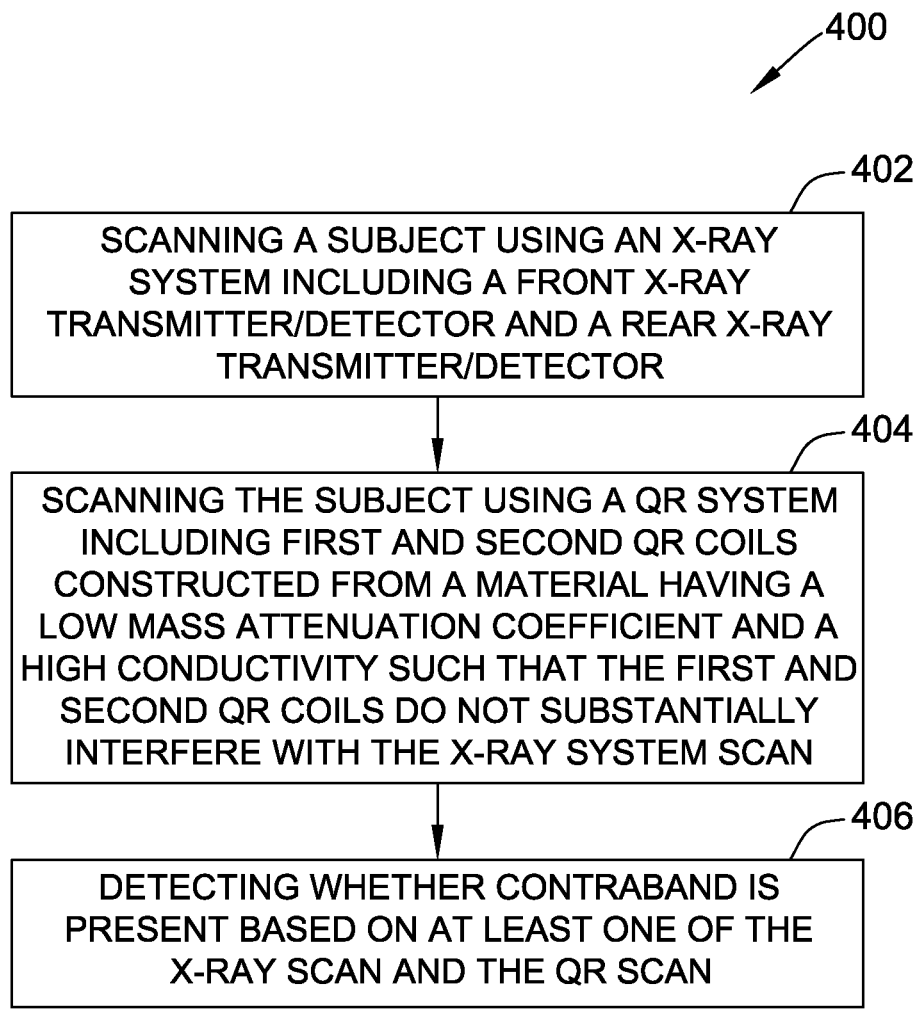
FIG. 4 is a flowchart of an exemplary method for detecting contraband.

FIG. 4 is a flowchart of an exemplary method 400 for scanning a subject, such as subject 220 (shown in FIG. 2) for contraband. The subject is scanned 402 using an X-ray system, such as X-ray system 102 (shown in FIG. 1). A QR system, such as QR system 104 (shown in FIG. 1), also scans 404 the subject. The QR system includes QR coils, such as QR coils 206 and 208 (both shown in FIG. 2) constructed from a material having a low mass attenuation coefficient and a high conductivity such that the coils do not substantially interfere with scanning 402 the subject with the X-ray system. In the exemplary embodiment, the X-ray scan and the QR scan are executed simultaneously. Accordingly, both scans can be executed while the subject is postured in a single position. Alternatively, the X-ray scan and the QR scan may be executed sequentially. Based on at least one of the X-ray scan and the QR scan, it is detected 406 whether contraband is present.

The embodiments described herein enable scanning a subject using both an X-ray system and a quadrupole resonance (QR) system. According to the systems and methods described herein, the X-ray system and QR system are essentially transparent to one another, and can be operated at the same time and be implemented in the same security scanner. Accordingly, as compared to at least some known contraband detection systems, the systems and methods described herein facilitate screening subjects more rapidly, while realizing benefits provided by both X-ray scanning and QR scanning.

A computer, such as those described herein, includes at least one processor or processing unit and a system memory. The computer typically has at least some form of computer readable media. By way of example and not limitation, computer readable media include computer storage media and communication media. Computer storage media include volatile and nonvolatile, removable and nonremovable media implemented in any method or technology for storage of information such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Combinations of any of the above are also included within the scope of computer readable media.

Exemplary embodiments of methods and systems for detecting contraband are described above in detail. The methods and systems are not limited to the specific embodiments described herein, but rather, components of systems and/or steps of the methods may be utilized independently and separately from other components and/or steps described herein.

Accordingly, the exemplary embodiment can be implemented and utilized in connection with many other applications not specifically described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A contraband detection system comprising:
   an X-ray system comprising:
      a front X-ray transmitter/detector;
      a rear X-ray transmitter/detector, wherein said front and rear X-ray transmitter/detectors are each configured to at least one of transmit X-rays and detect emitted photons to generate at least one image of a subject standing in a subject region;
   a quadrupole resonance (QR) system comprising:
      a first QR coil; and
      a second QR coil, wherein said first and second QR coils are located between said front and rear X-ray transmitter/detectors, and wherein said first and second QR coils are constructed from a material having a low mass attenuation coefficient and a high conductivity such that said first and second QR coils do not substantially interfere with transmitting X-rays and detecting emitted photons using said X-ray system; and
   a computing device coupled to said X-ray system and said QR system, said computing device configured to detect contraband at the subject region based on signals received from said X-ray system and said QR system.

2. A contraband detection system in accordance with claim 1, wherein at least one of said first and second QR coils is constructed from aluminum.

3. A contraband detection system in accordance with claim 1, wherein at least one of said first and second QR coils is constructed from carbon nanowires.

4. A contraband detection system in accordance with claim 1, further comprising:
   a first shield panel coupled to an interior face of said front X-ray transmitter/detector;
   a second shield panel coupled to an interior face of said rear X-ray transmitter/detector, wherein said first and second shield panels facilitate shielding said first and second QR coils from external interference.

5. A contraband detection system in accordance with claim 4, wherein at least one of said first and second shield panels is constructed from aluminum.

6. A contraband detection system in accordance with claim 4, wherein at least one of said first and second shield panels is constructed from carbon nanowires.

7. A contraband detection system in accordance with claim 1, wherein said first QR coil is located between said front X-ray transmitter/detector and the subject, and wherein said second QR coil is located between said front X-ray transmitter/detector and the subject region.

8. A contraband detection system in accordance with claim 1, wherein said first and second QR coils are both located between said front X-ray transmitter/detector and the subject region.

9. A contraband detection system in accordance with claim 1, wherein said first and second QR coils are both located between said rear X-ray transmitter/detector and the subject region.

10. A contraband detection system in accordance with claim 1, wherein said computing device is further configured to generate an alert when contraband is detected in the subject region.

11. A security scanner for detecting contraband located in or on a subject standing in a subject region, said security scanner comprising:
a front X-ray transmitter/detector;
a rear X-ray transmitter/detector, wherein said front and rear X-ray transmitter/detectors are each configured to at least one of transmit X-rays and detect emitted photons to generate at least one image of the subject;
a first QR coil; and
a second QR coil, wherein said first and second QR coils are located between said front and rear X-ray transmitter/detectors, and wherein said first and second QR coils are constructed from a material having a low mass attenuation coefficient and a high conductivity such that said first and second QR coils do not substantially interfere with transmitting X-rays and detecting emitted photons using said front and rear X-ray transmitter/detectors.

12. A security scanner in accordance with claim 11, wherein at least one of said first and second QR coils is constructed from aluminum.

13. A security scanner in accordance with claim 11, wherein at least one of said first and second QR coils is constructed from carbon nanowires.

14. A security scanner in accordance with claim 11, further comprising:
a first shield panel coupled to an interior face of said front X-ray transmitter/detector;
a second shield panel coupled to an interior face of said rear X-ray transmitter/detector, wherein said first and second shield panels facilitate shielding said first and second QR coils from external interference.

15. A security scanner in accordance with claim 11, wherein said first QR coil is located between said front X-ray transmitter/detector and the subject region, and wherein said second QR coil is located between said front X-ray transmitter/detector and the subject region.

16. A method for detecting contraband located on or in a subject, said method comprising:
scanning the subject using an X-ray system, wherein the X-ray system includes a front X-ray transmitter/detector and a rear X-ray transmitter/detector, the front and rear X-ray transmitter/detectors each configured to at least one of transmit X-rays and detect emitted photons to generate at least one image of the subject;
scanning the subject using a quadrupole resonance (QR) system, wherein the QR system includes a first QR coil, and a second QR coil, wherein the first and second QR coils are located between the front and rear X-ray transmitter/detectors, and wherein the first and second QR coils are constructed from a material having a low mass attenuation coefficient and a high conductivity such that the first and second QR coils do not substantially interfere with transmitting X-rays and detecting emitted photons using the X-ray system; and
detecting whether contraband is present based on at least one of the X-ray scan and the QR scan.

17. A method in accordance with claim 16, wherein said scanning the subject using an X-ray system and said scanning the subject using a QR system are performed substantially simultaneously.

18. A method in accordance with claim 16, wherein said scanning the subject using an X-ray system, and said scanning the subject using a QR system are performed with the subject postured in a single pose.

19. A method in accordance with claim 16, further comprising shielding the first and second QR coils from external interference using a first shield panel coupled to an interior face of the front X-ray transmitter/detector and a second shield panel coupled to an interior face of the rear X-ray transmitter/detector.

20. A method in accordance with claim 16, further comprising generating an alert when contraband is detected.

\* \* \* \* \*